(12) United States Patent
Shao et al.

(10) Patent No.: US 12,262,981 B1
(45) Date of Patent: Apr. 1, 2025

(54) VIRTUAL MICROWAVE PHANTOM GENERATION

(71) Applicants: Wenyi Shao, Laurel, MD (US); Todd McCollough, Barrington, IL (US)

(72) Inventors: Wenyi Shao, Laurel, MD (US); Todd McCollough, Barrington, IL (US)

( * ) Notice: Subject to any disclaimer, the term of this patent is extended or adjusted under 35 U.S.C. 154(b) by 986 days.

(21) Appl. No.: 17/327,450

(22) Filed: May 21, 2021

Related U.S. Application Data (60) Provisional application No. 63/036,291, filed on Jun. 8, 2020.

(51) Int. Cl.
*A61B 5/00* (2006.01)
*A61B 5/0507* (2021.01)
*A61B 5/055* (2006.01)

(52) U.S. Cl.
CPC ............ *A61B 5/0507* (2013.01); *A61B 5/055* (2013.01); *A61B 5/4312* (2013.01); *A61B 5/7267* (2013.01)

(58) Field of Classification Search
CPC ..... A61B 5/0507; A61B 5/055; A61B 5/4312; A61B 5/7267
See application file for complete search history.

(56) References Cited

U.S. PATENT DOCUMENTS

| | | | |
|---|---|---|---|
| 7,825,667 B2 | 11/2010 | Fang et al. | |
| 9,111,334 B2 | 8/2015 | McCollough et al. | |
| 9,386,936 B2 | 7/2016 | McCollough et al. | |
| 9,504,404 B1 | 11/2016 | Shao et al. | |
| 9,704,275 B2 | 7/2017 | McCollough et al. | |
| 9,869,641 B2 | 1/2018 | McCollough et al. | |
| 10,436,895 B2 | 10/2019 | Shao et al. | |
| 10,983,209 B2 | 4/2021 | Shao et al. | |
| 10,998,101 B1* | 5/2021 | Tran | A61B 5/486 |
| 2020/0330026 A1* | 10/2020 | Zhu | A61B 8/5207 |
| 2020/0364860 A1* | 11/2020 | Kearney | G16H 30/40 |
| 2021/0128070 A1* | 5/2021 | Kim | G06N 20/20 |

OTHER PUBLICATIONS

Shao ("Microwave Imaging by Deep Learning Network: Feasibility and Training Method", IEEE Transactions on Antennas and Propagation, vol. 68, No. 7 Jul. 2020, published on Mar. 12, 2020, pp. 5626-5635) (Year: 2020).*
Goodfellow ("Generative Adversarial Networks" Proceedings of the International Conference on Neural Information Processing Systems (NIPS 2014), pp. 2672-2680) (Year: 2014).*
Senaras et al., ("Optimized generation of high-resolution phantom images using cGAN: Application to quantification of Ki67 breast cancer images" PLOS ONE (May 9, 2018), pp. 1-12) (Year: 2018).*
Nikolova NK. Microwave imaging for breast cancer. IEEE Microw. Magzine. 2011; 12(7): 78-94.
Shao W, McCollough T. Advances in Microwave Near-Field Imaging: Prototypes, Systems, and Applications. IEEE Microwave Magazine. 2020; 21(5): 94-119.

(Continued)

*Primary Examiner* — Ping Y Hsieh (57) ABSTRACT

A method for generating virtual microwave (MW) phantoms at a specific MW frequency or multiple MW frequencies, comprising generating virtual MW phantoms using a generative neural network (generator) and identifying the authenticity of the virtual MW phantoms using a discriminative neural network (discriminator).

15 Claims, 4 Drawing Sheets

(56) References Cited

OTHER PUBLICATIONS

Ashtari A, et al. Using a priori information for regularization in breast microwave image reconstruction. IEEE Trans Biomed Eng. 2010; 57(9): 2197-2208.

Shao W, Pomper GM, Du Y. A learned reconstruction network for SPECT imaging. IEEE Trans Radiation Plasma Med Sci. 2021, 5(1): 26-34.

Shao W., Du Y. Microwave imaging by deep learning network: feasibility and training method. IEEE Trans Antennas Propag. 2020; 68(7): 5626-5635.

Hahn C, Noghanian S. Heterogeneous breast phantom development for microwave imaging using regression models. Inter J Biomed Imag. 2012; 2012: 1-12. Article ID 803607.

Joachimowica N, Conessa C, Henriksson T, Duchene B. Breast phantoms for microwave imaging. IEEE Antennas Wireless Propag Lett. 2014; 13: 1333-1336.

Goodfellow I, Pouget-Abadie J, Mirza M, Xu B, Warde-Farley D, Ozair S, Courville A, Bengio Y. Generative Adversarial Networks (PDF). Proceedings of the International Conference on Neural Information Processing Systems (NIPS 2014). pp. 2672-2680.

Radford A, Metz L, Chintala S. Unsupervised representation learning with deep convolutional generative adversarial networks. ICLR 2016 proceedings. 2016; 1-16.

Kazuhiro K, et al. Generative Adversarial Networks for the Creation of Realistic Artificial Brain Magnetic Resonance Images. Tomography. 2018; 4(4): 159-163.

Zastrow E, et al. Development of anatomically realistic numerical breast phantoms with accurate dielectric properties for modeling microwave interactions with human breast. IEEE Trans. Biomed Eng. 2008; 55(12):2792-2800.

Shao W, McCollough W. Multiple-GPU-based frequency-dependent finite-difference time domain formulation using MATLAB parallel computing toolbox. PIER. 2017; 72: 1-13.

Shao, W, Yong, D. SPECT Image Reconstruction by Deep Learning Using a Two-Step Training Method. JNM. 2019; 60 (supp. 1): 1353.

* cited by examiner

VIRTUAL MICROWAVE PHANTOM GENERATION

This application claims priority to U.S. Provisional Application No. 63/036,291, filed Jun. 8, 2020, whose entire contents are incorporated herein by reference.

BACKGROUND OF THE INVENTION

The present disclosure pertains generally to digital medical phantom generation, more specifically, using artificial intelligence (AI) technology to generate virtual medical phantoms for use in medical imaging, including microwave (MW) breast imaging.

MW breast imaging is an alternative method to mammography, and benefits patients because both ionizing radiation and breast compression are avoided, resulting in safer and more comfortable exams. MW breast imaging's inexpensive cost makes it very likely to become a regular exam tool adopted in small hospitals and small clinics in the near future. Unlike a computed tomography (CT) image showing tissue density in the breast, an image reconstructed by the MW technique is usually a dielectric-parameter distribution in the breast, e.g., the dielectric constant, or the permittivity. Studies have shown that at MW frequencies, the dielectric parameters of malignant breast tumors are significantly higher than those of normal breast tissues. These advantages allow MW breast imaging to become a future diagnostic tool in breast cancer detection and monitoring. However, its progress toward widespread clinical application would greatly benefit from an improvement to its relatively low spatial resolution (centimeter level), especially in comparison with established modalities such as positron emission tomography (PET) and magnetic resonance imaging (MRI).

Substantially improving the spatial resolution can be found today by AI technologies. A solution from AI does not need to be 100% relied on measurement data alone, but also based on the experience attained by the machine when it is learning the logic during training. In the art of AI-based medical imaging, high-quality images are expected to be obtained from the output of the neural network, when given the measurement data collected from the clinic or simulation as input. In the development of such an AI system, high-accurate images (high resolution, low noise, high contrast, etc.) are required to serve as the image label (also named "ground truth") to train the neural network. Then, when using the developed network to reconstruct an image, the obtained image is supposed to match the quality of those used in training and is therefore improved from what is produced by conventional reconstruction approaches. However, the ground truth is unknown in practice (unavailable in the real world). Existing AI medical imaging techniques often use reconstructed images from conventional methods as the label to train the neural network. As a result, the aim was merely to develop a rapid imaging tool (AI can reconstruct an image at mm-sec level, which is very comparable to conventional approaches requiring hours) with the image quality matching the conventional approach, rather than providing a better image. This would undermine the potential of AI methods. To fully realize the potential of AI in medical imaging, accurate phantoms used as known truth, is desirable to guide the training.

Ideally, the phantom datasets should include all possible scenarios (i.e., clinic) in order to prevent from overfitting (meaning the AI system only fits well to the training data instead of providing a solution to a general problem) that often occurs in the design of neural networks. Famous AI systems such as GoogLeNet and Inception-v3 that have been demonstrated to successfully identify natural images were all trained with millions of images. However, most of the published studies in medical imaging often use only a small set of training data (a few tens of patients). These systems are very likely overfitted to the limited data used in training, causing reduced reliability. In order to have accurate and sufficient data to train an AI system for MW breast imaging, the present invention discloses a method to generate such data to support the development of an AI-based imaging system.

SUMMARY OF THE INVENTION

The present inventive concepts belong to medical imaging. Data generated by the inventive approach can be used to support, but is not restricted to, AI-based MW breast imaging. MW is a type of non-ionizing radiation and may potentially be used as a non-invasive medical tool to diagnose many diseases, of which the most promising one is MW breast cancer detection. The physics explanation as to why MW can perform this job is that the dielectric properties of cancerous tissue are significantly different (0.1~10 times larger) than those of normal breast tissue at MW frequencies, which may result in a high-contrast image. More importantly, the radiation dose for a regular breast examination is equivalent to using a wireless phone, meaning that it is much safer than most of the other medical imaging modalities—many nuclear medicine modalities (ionizing radiation) are cancer-inducing themselves. Hence, repeatable MW exams within a short time period is allowed with no safety concerns, which means tumors growing very fast would not miss the best treatment time window. Lastly, the inexpensive cost of MW breast examinations further enables its feasibility to become a routine tool for breast health monitoring. The current challenge for MW breast detection is that breast tissues are lossy media and the loss increases with MW frequency. To allow sufficient MW penetration into the breast (80% breast tumor exists in 0~50 cm depth), the operating frequency has to be restricted up to a few gigahertz (GHz). With such frequency, only a centimeter-level spatial resolution can be achieved, which is far from ideal. Although many advanced algorithms have been applied to improve the imaging resolution, the resolution is still much poorer than those high-quality medical imaging modalities such as PET (mm level) and MRI (better than 1 mm).

Recent achievements in deep neural networks (NN) for emission tomography implies that the cutting-edge deep learning (DL) algorithm is likely to be an effective tool to significantly improve the MW imaging resolution. However, to conduct this job, a large number of digital breast phantoms serving as the image label (also named "ground truth") are required. An existing MRI breast phantom can be easily converted to a dielectric breast phantom with algorithms. However, a large breast phantom population (ideally millions) is very difficult to acquire from practice. Therefore, the current disclosure presents a method that uses generative adversarial network (GAN) to generate artificial breast phantoms that are very similar to realistic human breasts, for, but not limited to, the use in MW medical imaging.

GAN is a kind of neural network that can generate images with similar characteristics as the images provided in training. With the limited number of real human breast phantoms, one may generate as many digital breast phantoms as needed from the GAN. The generated phantoms can be used to perform simulation(s) for MW breast cancer detection, and, in conjunction with the electric fields generated from the simulation(s), be used as the ground truth to train a neural network for image reconstruction. Data collected from a clinic, doctor's office, hospital, or other acquisition site can then be input to the trained neural network to produced a reconstructed MW image. A diagnosis of whether or not the patient has breast cancer can then be made.

More than generating dielectric breast phantoms for MW imaging, the concept disclosed in this invention can be also used to generate breast phantoms for other medical imaging modalities such as MRI and CT for researches with AI related or not related. The method is also applicable to generate other human organ phantoms to support medical research such as for cardiac imaging, knee injury detection, and brain disorder diagnosis, where large numbers of phantom data are needed.

BRIEF DESCRIPTION OF THE DRAWINGS

Embodiments will now be described in more detail with reference to the accompanying drawings, given only by way of example, in which.

DETAILED DESCRIPTION OF EMBODIMENTS OF THE INVENTION

GAN is a type of deep neural network that can generate data with similar characteristics as the given training data, initially described by Goodfellow, I. et al, "Generative Adversarial Networks. Proceedings of the International Conference on Neural Information Processing Systems," NIPS 2014, pp. 2672-2680, which is herein incorporated by reference. GAN has been primarily applied in the past to generating artificial natural images and human-face images. A GAN consists of two networks that train together: first, the generator, a network that generates data, given a set of random values as the input; second, the discriminator, a network that evaluates the data for authenticity, i.e., it attempts to classify the observation belonging to "real" or "generated". By alternately training the generator network and the discriminator network, at the end of training, the discriminator has learned to identify characteristics in the training data, while the generator is able to generate near realistic data, which very similar in quality to the training data. Technically, two networks are trained simultaneously to maximize the general performance:

a. Train the generator to generate data that attempts to fool the discriminator by maximizing the loss function of the discriminator. That is, the objective of the generator is to generate data classified as "real" by the discriminator.

b. Train the discriminator to distinguish between real and generated data by minimizing the loss of the discriminator when given batches of both real and generated data. That is, the objective of the discriminator is to not be fooled by the generator.

Mathematically, the generator is like a special function that can integrate a set of randomly distributed numbers in the number axis to a particular region in number axis with implicit rules hidden in the network. Compared to the variational autoencoder, another technique which can also generate artificial images, GAN is able to generate much larger and more complex images.

In MW breast imaging, pixels in the image usually represents the average permittivity or conductivity value (of the tissue) in the voxel at a specific frequency. In order to apply high accurate images (as the image label) to guide the training of AI-based image reconstruction, dielectric images (permittivity or conductivity) converted from MRI images can be used to achieve high resolution. Prior such MRI images to dielectric images conversion techniques are previously known in the art such as in Zastrow E. et al., "Development of anatomically realistic numerical breast phantoms with accurate dielectric properties for modeling microwave interactions with human breast", IEEE Trans. Biomed Eng. 2008, 55 (12): 2792-2800, which is herein incorporated by reference. After conversion, the obtained high-resolution dielectric breast phantoms are used as the training data (serving as "real breast phantom") to develop the GAN.

Figure 1:
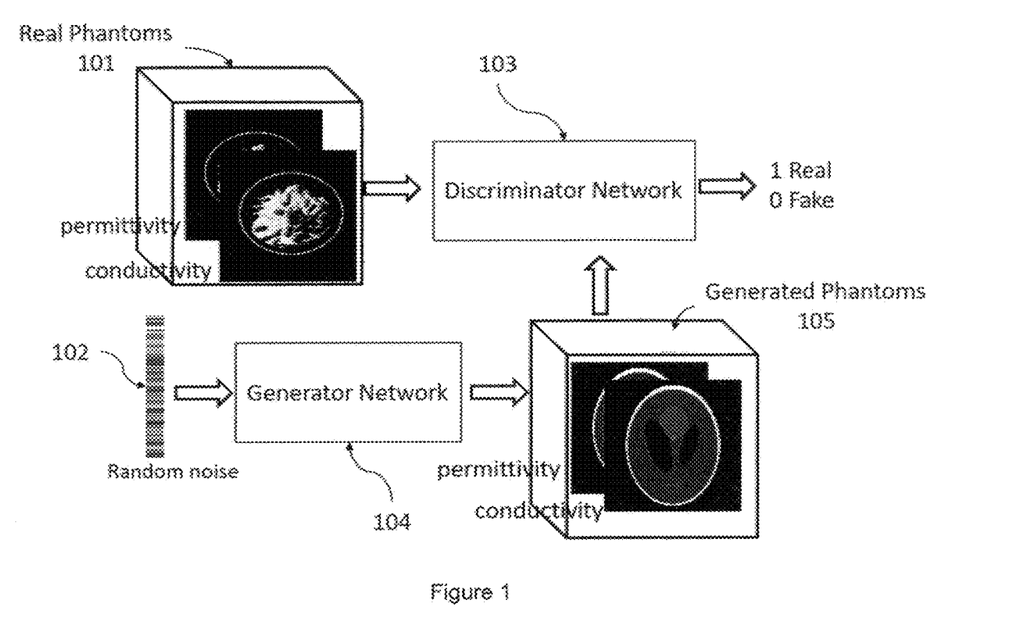
FIG. 1 shows the training method of GAN for generating digital breast phantoms, including one permittivity image and one conductivity image from a set of permittivity and conductivity images at a specific MW frequency.

Referenced by the scheme shown in FIG. 1, the steps to train a GAN for the purpose of generating dielectric breast phantoms are:

1) Initialize the learnable parameters in the generator 104 and the discriminator 103, then give a set of random numbers 102 to the generator 104 to produce some artificial generated phantoms 105. At this point, the artificial generated phantoms 105 are very different from the real phantoms 101 (each dielectric breast phantom is denoted by a permittivity image and a conductivity image, after being converted from a MRI breast phantom). Instead of calling 105 artificial generated phantoms, the artificial generated phantoms are more like junk images;

2) Import both the artificial generated phantoms 105 and real phantoms 101 into the discriminator 103, and use label 1 and 0 to represent real and fake (generated), respectively, to train the discriminator 103. This is a simple classification problem which only has two categories of outputs: 1 (real) or 0 (fake);

3) As the training of the discriminator 103 completes, connect the generator 104 and the discriminator 103 (the generator 104 is followed by the discriminator 103); fix the learnable parameters in the discriminator 103 and update the learnable parameters in the generator 104 only. Since the desire is to have the generator 104 produce meaningful phantoms, the output label of the connected network is always set to 1 (real) during this training step;

4) Use the updated generator 104 to produce some artificial phantoms, then repeat step 2 (above) to train the discriminator 103, and repeat step 3 (above) to train the generator 104, until the generator 104 can generate acceptable breast phantoms.

The generator 104 and the discriminator 103 are trained alternately. When a sufficient number of iterations have been executed, the discriminator 103 has learnt the ability to refine breast phantoms out from other images, while the generator 104 has learnt strong characteristics of the source data and can generate breast phantoms very similar to real phantoms. Neural network training of the GAN, may use any optimization algorithm such as ADAM or stochastic gradient descent with momentum (SGDM). The generator cost function tends to drop when the training is undergoing, accompanied with oscillations. Theoretically, when the cost value approaches a user-prespecified value (usually small, such as 0.0001), it is a good sign to end the training. However, many GAN training examples have shown that the output image instead begins to worsen after a certain point when the cost function value continues dropping. Therefore, the training of the GAN may terminate early according to human observation. Hence, there is a demand for the generator to output some generated image examples every few epochs (iterations) during the training, for the ease making a potential decision on ending the training.

Figure 2:
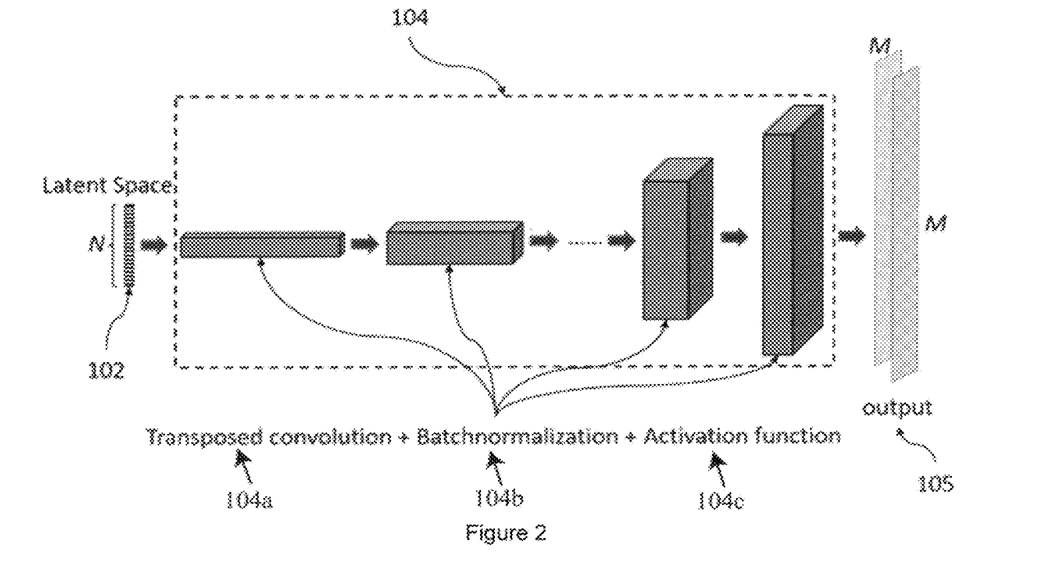
FIG. 2 is the architecture of the generator network.

The network architecture of the generator 104 is presented in FIG. 2. The generator 104 is formed by a plurality of transposed convolutional layers 104a (may be replaced or partly replaced by fully-connected layers), with each followed by a batch normalization layer 104b and then a non-linear activation function 104c, such as ReLu function or hyperbolic tangent function. The input of random numbers 102 of the generator 104 is composed of N random numbers (from the "latent space" called in some literatures). When random numbers 102 passes through the generator 104, an M-by-M image of the artificial generated phantoms 105 can be obtained from the output of the generator 104. Note that the artificial generated phantoms 105 can also be a plurality of M-by-M images when the generator 104 is designed to have a plurality of output channels. For example, the generator 104 can be designed to generate a permittivity image and a conductivity image simultaneously (two output channels), for a specific MW frequency, i.e., the real phantoms 101 (and the artificial generated phantoms 105), where one permittivity image and one conductivity image are bundled denoting one breast phantom.

Figure 3:
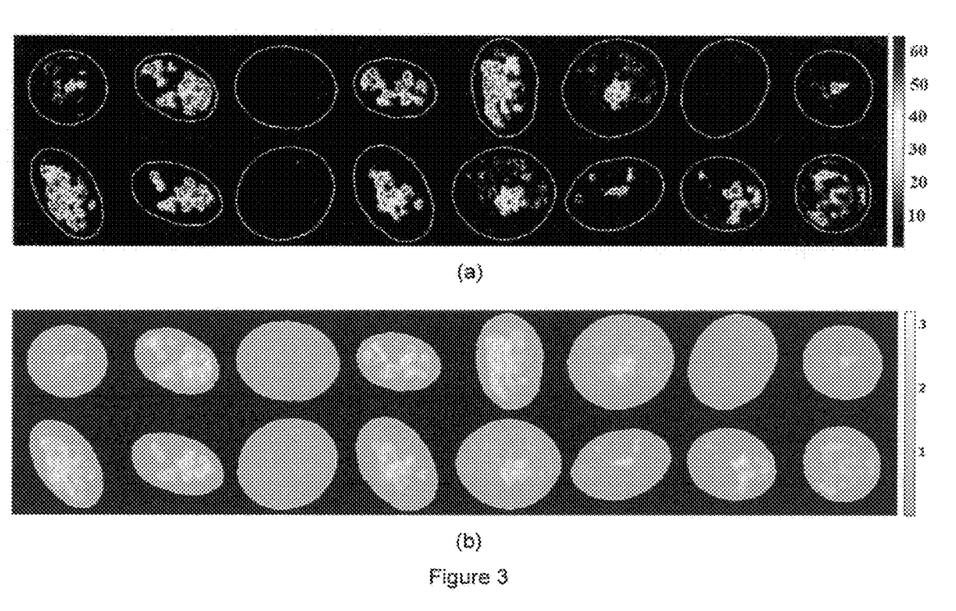
FIG. 3 shows generated breast phantoms at 3 GHz by a GAN: (a) images showing the distribution of permittivity in the breast and (b) images showing the distribution of conductivity in the breast.

FIG. 3 shows some generated breast phantoms 105 from a single generator, where (a) shows images of the permittivity distribution and (b) shows images of the conductivity distribution in the breast for 3 GHz. These images are representative of the types of phantoms that can be generated but are not limited to a breast and are not limited to a frequency at 3 GHZ. Other frequencies and other body regions can be used for the generated phantoms.

Figure 4:
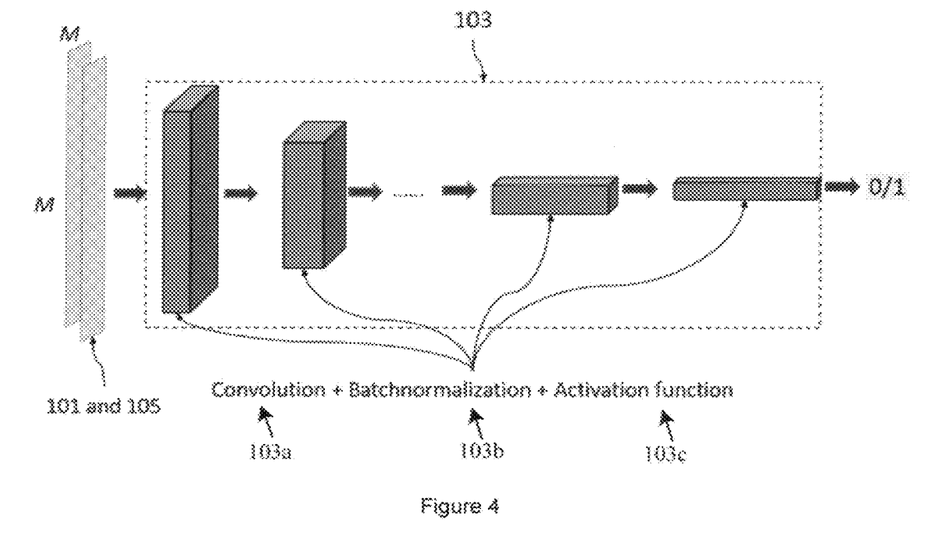
FIG. 4 is the architecture of the discriminator network.

The network architecture of the discriminator 103 is presented in FIG. 4. The discriminator 103 is formed by a plurality of convolutional layers 103a (may be replaced or partly replaced by fully-connected layers), with each followed by a batch normalization layer 103b and then a non-linear activation function 103c, such as ReLu or leaky ReLu function. When the real phantoms 101 or artificial generated phantoms 105 passes through the discriminator 103, the output will show the input image as real or "fake" (generated) after training. Note that the input can have a plurality of channels to accept different types of dielectric images simultaneously. When this is the case, the discriminator 103 will also consider the correlation between the images from different channels before making a judgement.

The objective of the generator is to fool the discriminator such that it allows the generated data to be classified as "real". To maximize the probability that the generated images are identified as "real" by the discriminator, a loss function to minimize the negative log likelihood function can be used:

$$\text{Loss}G = -\text{mean}(\log(\Omega(\hat{Y}_g)))$$

where $\Omega$ denotes the sigmoid function, and $\hat{Y}_g$ denotes the output of the discriminator with generated data input. The objective of the discriminator is to not be fooled by the generator. To maximize the probability that the discriminator successfully discriminates between real and generated phantoms, minimize the sum of the corresponding negative log likelihood function. Thus, the loss function for the discriminator is given by:

$$\text{loss}D = -\text{mean}(\log(\sigma(\hat{Y}_r)) - \text{mean}(\log(1-\sigma(\hat{Y}_g))))$$

where $\hat{Y}_r$ denotes the output of the discriminator with real data input. During the early stage of training, it can be observed the loss of the generator and the discriminator keeps reducing but is accompanied with oscillations. After certain iterations of training, the losses cease to reduce, although the oscillations continue. At this point, the training has to be ended manually to prevent the generated images from becoming worse instead of better as the training continues.

In order to allow the pixel values in the generated image to only fall in a reasonable region, the training data have to be normalized according to the span of the output of the last activation function in the generator. For example, if the last activation function is a hyperbolic function (output range −1 to 1), the pixel values in the training images will all be converted into such region, linearly or nonlinearly. Then, when the developed generator was used to generate phantoms, the output data (values between −1 to 1) will be converted back to the region in which the breast dielectric parameters belong to. The normalization technique helps converge the neural networks better during the training.

Figure 5:
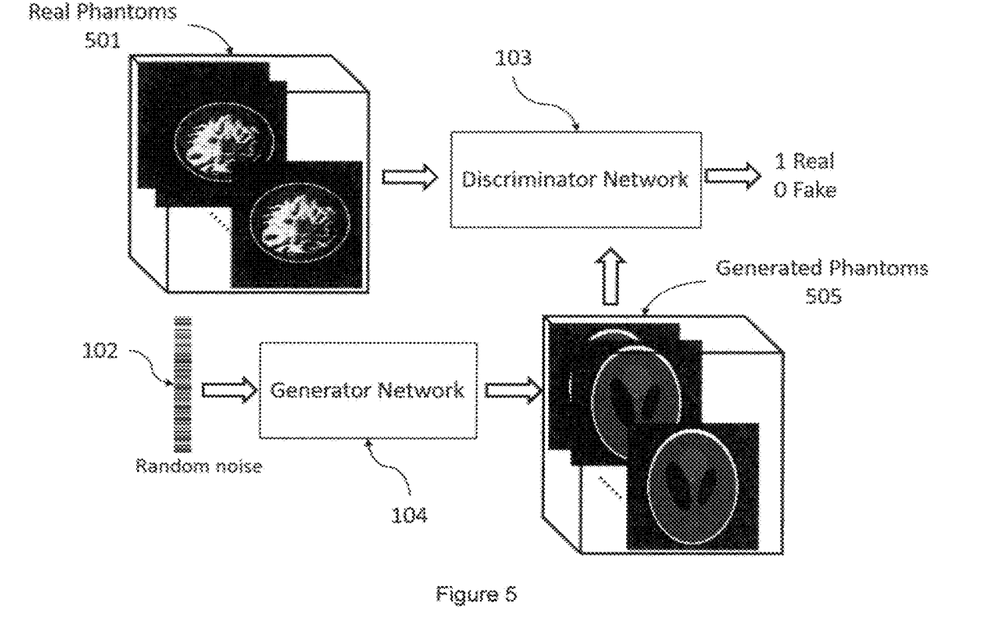
FIG. 5 shows the training method of GAN for generating digital breast phantoms for multiple MW frequencies for a wideband MW study, where each phantom includes a plurality of images with each representing a parameter in the Cole-Cole equation.

When the GAN is designed to generate breast phantoms for a multiple-frequency MW imaging study, in the frequency domain or in the time domain, a dielectric breast phantom consisting of more images can be generated from one generator, and these images bundled together are fed to the discriminator for considering the phantom's authenticity. As an example, the single-pole Cole-Cole model is used to denote the frequency dependence of breast tissue dielectric properties:

$$\hat{\varepsilon}(\omega) = \varepsilon_\infty + \frac{\varepsilon_s - \varepsilon_\infty}{1 + (j\omega\tau)^{1-\alpha}} + \frac{\sigma_s}{j\omega\varepsilon_0}$$

where $\hat{\varepsilon}$ is the complex dielectric constant, $\omega$ is the angular frequency defined as $\omega=2\pi f$ (f is the frequency), $\varepsilon_0$ is the vacuum permittivity, $\varepsilon_\infty$ is the distribution of the permittivity at infinite high frequency in the breast, $\varepsilon_s$ is the is the distribution of the permittivity at static frequency in the breast, $\tau$ is the distribution of principal relaxation time of the dipole rotation in the breast, $\sigma_s$ is the distribution of the conductivity at static frequency in the breast, and $\alpha$ is a relaxation parameter. The five parameters $\varepsilon_\infty$, $\varepsilon_s$, $\sigma_s$, $\tau$, and $\alpha$ are the fitting parameters, thus there will be a set of five output images for each breast phantom, with each representing the distribution of one parameter in the breast, from the generator. With the five images, one may use the above Cole-Cole equation to acquire a complex-permittivity breast phantom at any specific MW frequency (within the effective spectrum, such as 3 to 10 GHz), or perform a wide-band MW breast imaging study in the time domain, such as by using the multiple-frequency finite-difference time-domain method. Therefore, a generator designed to produce breast phantoms for a multi-frequency/wideband MW study must have multiple output channels, and the corresponding discriminator must have multiple input channels, which is different from the GAN designed for single-frequency study (where it is optional to have one or multiple channels, i.e., a permittivity image and/or a conductivity image). However, it is optional to fix one or more parameters of the five parameters $\varepsilon_\infty$, $\varepsilon_s$, $\sigma_s$, $\tau$, and $\alpha$ (for example, set $\alpha=0$, then the Cole-Cole model reduces to the Debye model, and/or fix the value of $\tau$), then the generator will have a reduced number of output channels (each output image represents the distribution of one parameter in the breast). But usually no more than two parameters of the five are fixed since this leads to limited variables in the Cole-Cole equation, reducing accuracy. FIG. 5 illustrates a GAN to generate digital breast phantoms for multiple frequency or wideband use. Multiple output channels of artificial generated phantoms 505 for the generator and multiple input channels real phantoms 501 for the discriminator are required.

The technique of designing such a GAN for generating multiple-frequency MW breast phantoms, including the training procedures and neural network structure, is similar as the one for generating a single-frequency MW breast phantoms, as previously introduced and described with respect to FIGS. 1, 2, and 4. The differences are just that the training data will be the fitting parameters (or subset of the fitting parameters) in the Cole-Cole equation, and the output of the generator and the input of the discriminator are both a set of images showing the distribution of those fitting parameters in the breast.

The MW breast phantom discussed in this invention may be extended to 3-D phantoms. As such, a 3-D GAN, comprising a generator that adopts 3-D transposed convolutional computation and a discriminator that adopts 3-D convolutional computation, is used to generate 3-D artificial MW breast phantoms.

In an alternative embodiment of the invention a GAN is designed to generate MRI breast phantoms directly (T1 and/or T2 weighted) using the real MRI breast phantoms as the training data, then the generated MRI phantoms are also converted to dielectric breast phantoms. The technique of designing such a GAN for generating MRI breast phantoms, including the training procedures and network structure, is similar as the one for generating MW breast phantoms, as previously introduced and described. The differences are that the MRI images will be used as the training data (no conversion to dielectric data), and the output of the generator, as well as the input of discriminator, would be MRI phantoms. The advantage of this alternative embodiment is that the generated MRI breast phantoms are not limited to conversion just dielectric phantoms, but can also be converted to phantoms for other medical applications. The disadvantage of this alternative embodiment is that, there is often demand to produce a large phantom population with the developed GAN, thus the number of generated phantoms is much larger than the number of source phantoms (training data). Therefore, the computational time for the phantom conversion to dielectric data will be increased.

Figure 6:
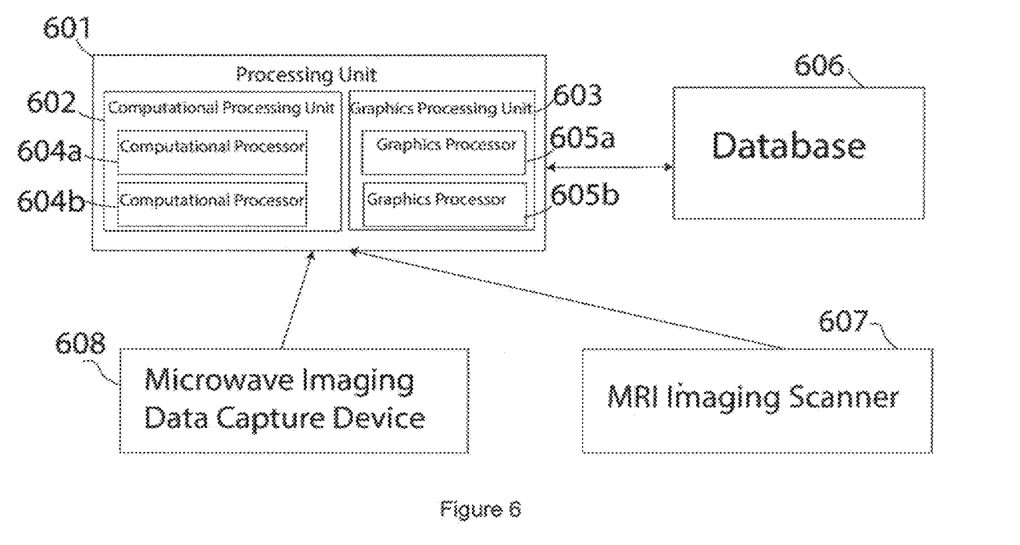
FIG. 6 illustrates a schematic of the system used for generating digital phantoms according to an embodiment of the invention.

FIG. 6 illustrates a schematic of the system used for generating digital phantoms according to an embodiment of the invention. This system is applicable for generating digital breast phantoms but is also applicable to generate other human organ phantoms where large numbers of phantom data are needed. The GAN is trained using a processing unit 601. In an embodiment the GAN is trained using a computational processing unit 602 and graphics processing unit 603, both part of the processing unit 601. In other embodiments the processing unit 601 contains only a computational processing unit 602 or contains only a graphics processing unit 603. In an embodiment the computational processing unit 602 contains a plurality of computational processors 604a and 604b. In an embodiment the graphics processing unit 603 contains a plurality of graphics processors 605a and 605b. In some embodiments the computational processing unit 602 contains a single computational processor 604a and the graphics processing unit contains a single graphics processor 605a. In some embodiments the computational processing unit 602 and graphics processing unit 603 can operate in parallel with each other or within themselves and their respective processors. The processing unit 601 is connected to a database 606 which is searchable based on patient characteristics. These patient characteristics can include for example age, sex, weight, height, geographic origin, ethnicity, and body region or body part of the scan. In some embodiments the database 606 is a plurality of databases. The database 606 contains a plurality of previously collected and reconstructed MRI images. In other embodiments the database 606 contains a plurality of previous collected reconstructed images from other imaging modalities including single-photon emission computerized tomography (SPECT), PET, CT, x-ray, or ultrasound. The processing unit 601 is further configured to convert previously collected and reconstructed MRI images contained in the database to dielectric images including permittivity images and conductivity images. In other embodiments the data is collected using an MRI imaging scanner 607 and then the reconstructed MRI images are sent to the database 606.

The virtual realistic microwave phantoms generated by the GAN are stored in the database 606. Each virtual realistic microwave phantom from the set of virtual realistic microwave phantoms are individually used as the permittivity and conductivity in computational electromagnetic simulations carried about by the processing unit 601 to generate the electric fields such as using Method of Moments (MoM) or Finite-Difference Time-Domain method (FDTD). Each virtual realistic microwave phantom from the set of virtual realistic microwave phantoms are also used as the five parameters of the Cole-Cole model (or a subset of these five parameters) in computational electromagnetic simulations carried about by the processing unit 601 to generate the electric fields using multiple-frequency finite-difference time-domain method. These generated electric fields from the virtual realistic MW phantoms are used in conjunction with another neural network to develop a reconstruction algorithm to predict cancer or other disease states. In some embodiments the type of cancer is breast cancer and the other disease states include brain stroke, cardiovascular disease, or a tear in a ligament in the knee. The additional neural network is trained using the processing unit 601 using the generated electric fields as the input and the virtual realistic microwave phantoms as the output. Next, data is collected using a microwave imaging data capture device 608 to collect electric fields. Types of microwave imaging data capture devices 608 are previously known in the art and for example described in W. Shao and T. McCollough, "Advances in Microwave Near-Field Imaging: Prototypes, Systems, and Applications," IEEE Microwave Magazine, vol. 21, no. 5, pp. 94-119, May 2020, which is herein incorporated by reference. The microwave data capture device can collect data at a single data acquisition site or a plurality of data acquisition sites. The data acquisition site(s) may be remote from the processing unit 601 and/or database 606. These collected fields are input to the additional neural network to form a prediction of the reconstructed dielectric image. Based on the permittivity and conductivity of the reconstructed dielectric image and knowledge of normal and healthy tissue dielectric values predictions can be made about the disease state.

Figure 7:
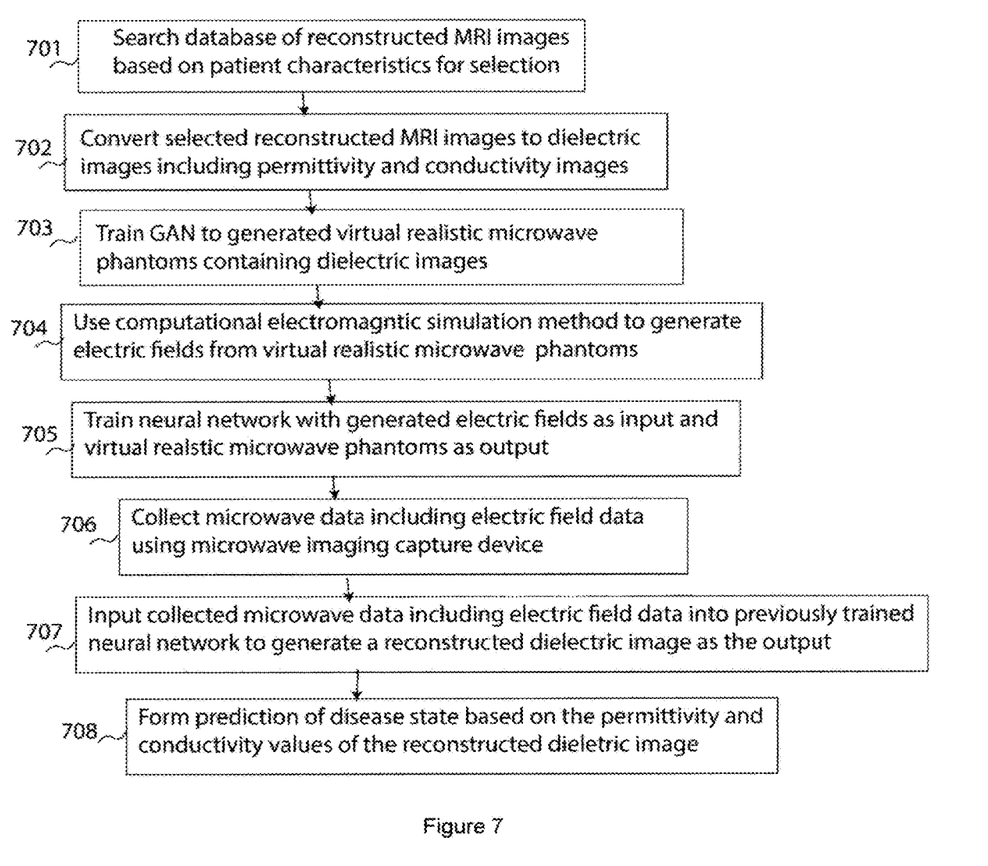
FIG. 7 is a flowchart of exemplary steps used for reconstructing a MW image based on using GAN for generating digital phantoms according to an embodiment of the inventive concepts disclosed herein.

FIG. 7 illustrates a flowchart of exemplary steps used for reconstructing a MW image based on using a GAN for generating phantoms according to an embodiment. In step 701 a database or plurality of databases is searched based on patient characteristics to select previously reconstructed MRI images. In step 702, the selected reconstructed MRI images from step 701 are converted to dielectric images including permittivity and conductivity images. In step 703, the converted dielectric images from step 702 are used to train a GAN to generate virtual realistic microwave phantoms. In various embodiments this training is carried out using the steps previously described in conjunction with the description of FIG. 1 or 5. In some embodiments the virtual realistic microwave phantoms are at specific MW frequency. In other embodiments the virtual realistic microwave phantoms are wideband and cover a plurality of MW frequencies. In step 704, the generated virtual realistic microwave phantoms from step 703 are input to a computational electromagnetic simulation (each virtual realistic microwave phantom from the set of virtual realistic microwave phantoms input individually) method to generate electric fields. In an embodiment the computational electromagnetic simulation method is MoM. In another embodiment the computational electromagnetic simulation method is FDTD. In step 705, the generated electric fields from step 704 serve as input to a neural network and the generated virtual realistic microwave phantoms from step 703 serve as output to the neural network that is trained. In some embodiments the neural network is trained using a gradient descent algorithm. In other embodiments the neural network is trained using an evolutionary optimization algorithm such as particular swarm optimization. In some embodiments the neural network is trained using a combination of training algorithms. In step 706, a microwave data capture device collects microwave data including electric field data. In an embodiment the microwave data capture device scans a patient or body region of a patient. In step 707, the collected microwave data including electric field data from step 706 is input to the previously trained neural network from step 705 in order to generate a reconstructed dielectric image as the output. In step 708, the reconstructed dielectric image from step 707 is analyzed and a diagnosis is made about the disease state. In an embodiment the diagnosis is whether or not the patient has breast cancer. In another embodiment the diagnosis is whether or not the patient is suffering from a stroke. In another embodiment the diagnosis is whether or not the patient is suffering from cardiovascular disease. In another embodiment the diagnosis is whether or not the patient has a tear in tissue of the knee.

The invention is not limited to the specific embodiments herein and it will be understood by those skilled in the art that variations and modifications can be effected within the sprit and scope of the inventive concepts.

We claim:

1. A method for generating virtual microwave (MW) phantoms at a specific MW frequency, comprising:
   generating virtual MW phantoms using a generative neural network (generator);
   identifying the authenticity of the virtual MW phantoms using a discriminative neural network (discriminator);
   wherein the generator is configured to generate virtual permittivity images or conductivity images at the specific MW frequency;
   wherein the discriminator is configured to evaluate input permittivity images or conductivity images at the specific MW frequency;
   selecting reconstructed MRI images from a searchable database of a plurality of reconstructed MRI images based on patient characteristics; and
   converting the selected reconstructed MRI images to the input permittivity images or conductivity images at the specific MW frequency.

2. The method of claim 1, further comprising training the generator and the discriminator in an alternative manner until a stopping criterion is reached wherein the virtual MW phantoms generated by the generator are realistic.

3. The method of claim 2, wherein training the generator and the discriminator occurs using at least one of a plurality of computational processors or graphics processing units operating in parallel.

4. The method of claim 2, further comprising generating electric fields from the virtual realistic MW phantoms using computational electromagnetic simulations.

5. The method of claim 4, further comprising training a neural network using the generated electric fields as input and the virtual realistic MW phantoms as output.

6. The method of claim 5, further comprising:
   receiving collected electric fields; and
   inputting the received collected electric fields to the neural network to reconstruct at least one permittivity image or conductivity image at the specific MW frequency.

7. A method for generating virtual microwave (MW) phantoms at a specific MW frequency, comprising:
   generating virtual MW phantoms using a generative neural network (generator);
   identifying the authenticity of the virtual MW phantoms using a discriminative neural network (discriminator);
   wherein the generator comprises a plurality of transposed convolutional layers, batch normalization layers, and non-linear activation functions and wherein the discriminator comprises a plurality of convolutional layers, batch normalization layers, and non-linear activation functions.

8. The method of claim 7, wherein at least a subset of the transposed convolutional layers are replaced by fully-connected layers.

9. A method for generating virtual microwave (MW) phantoms at multiple MW frequencies, comprising:
   generating virtual MW phantoms using a generative neural network (generator);
   identifying the authenticity of the virtual MW phantoms using a discriminative neural network (discriminator);
   wherein the generator is configured to simultaneously generate a set of wideband MW images for each virtual MW phantom of the MW phantoms at the multiple MW frequencies; wherein the set of MW images comprises:
   an image showing the distribution of the permittivity ($\varepsilon_\infty$) at infinite high frequency;
   an image showing the distribution of the permittivity ($\varepsilon_s$) at static frequency; and
   an image showing the static conductivity ($\sigma_s$) at static frequency.

10. The method of claim 9, wherein the set of wideband MW images further comprises: an image showing the distribution of relaxation parameter a; and an image showing the distribution of principal relaxation time (τ) of dipole rotation.

11. The method of claim 9, wherein the discriminator is configured to evaluate input permittivity images or conductivity images at the multiple MW frequencies.

12. The method of claim 9, wherein the virtual MW phantoms are virtual 3-D MW breast phantoms.

13. A method for generating virtual microwave (MW) phantoms, comprising:
  generating virtual MRI phantoms using a generative neural network (generator);
  identifying the authenticity of the virtual MRI phantoms using a discriminative neural network discriminator
  converting the virtual MRI phantoms to virtual MW phantoms;
  training the generator and the discriminator in an alternative manner until a stopping criterion is reached wherein the virtual MRI phantoms generated by the generator are realistic and hence conversion to virtual MW phantoms is realistic;
  generating electric fields from the virtual realistic MW phantoms using computational electromagnetic simulations; and
  training a neural network using the generated electric fields as input and the virtual realistic MW phantoms as output.

14. The method of claim 13, further comprising:
  receiving collected electric fields from at least one data acquisition site; and
  inputting the received collected electric fields to the neural network to reconstruct at least one of (1) a permittivity image and conductivity image at a specific MW frequency or (2) a set of wideband MW images showing the distribution of permittivity and conductivity at a plurality of MW frequencies.

15. The method of claim 13, further comprising:
  selecting reconstructed MRI images from a searchable database of a plurality of reconstructed MRI images based on patient characteristics; and
  wherein the discriminator is configured to evaluate the selected reconstructed MRI images.

* * * * *